United States Patent [19]

Henkart et al.

[11] Patent Number: 5,607,831
[45] Date of Patent: Mar. 4, 1997

[54] IN VITRO METHODS FOR ASSESSING THE SUSCEPTIBILITY OF HIV-1-INFECTED INDIVIDUALS TO CYSTEINE PROTEASE-MEDIATED ACTIVATION-INDUCED PROGRAMMED CELL DEATH

[75] Inventors: Pierre Henkart, Annapolis; Apurva Sarin; Mario Clerici, both of Rockville; Gene M. Shearer, Bethesda, all of Md.

[73] Assignee: The United States of America as represented by the Department of Health and Human Services, Washington, D.C.

[21] Appl. No.: 37,578

[22] Filed: Mar. 25, 1993

[51] Int. Cl.$^6$ ............................ C12Q 1/70; G01N 33/53; G01N 33/555; G01N 33/567
[52] U.S. Cl. ........................ 435/5; 435/7.24; 435/23; 435/219
[58] Field of Search ........................ 435/5, 7.24, 7.4, 435/6, 23, 219

[56] References Cited

FOREIGN PATENT DOCUMENTS 395309 10/1990 European Pat. Off. .

OTHER PUBLICATIONS

Schwartz, R., "Autoimmunity and autoimmune diseases", in Fundamental Immunology, Paul, ed., Raven Press, New York, 1993, pp. 1033–1098.
Murachi et al., "A Quantitative Distribution Study on Calpain and Calpastatin in Rat Tissues and Cells", *Biochem. Int.* 2: 651 (1981).
Hanada et al., "Characterization of the Three New Analogs of E-64 and Their Therapeutic Application", *Proteinase Inhibitors: Medical and Biological Aspects*, Katunuma, ed., Springer-Verlag, Tokyo, pp. 25–36 (1983).
Amamoto et al., "Effect of E-64, a Thiol Protease Inhibitor, on Antibody Formation in Mice", *Biochem. Biophys. Res. Comm.* 118: 117 (1984).
Adachi et al., "Distribution and Expression of Calpastatin in Human Hematopoietic System Cells", *Biol. Chem.* 369:223–227 (May, 1988).
Murachi, "Intracellular Regulatory System Involving Calpain & Calpastatin" *Biochem. Int.* 18: 263–294 (1989).
Mercep et al., "The Cell Cycle Block and Lysis of an Activated T Cell Hybridoma are Distinct Processes with Different Ca$^{2+}$ Requirements and Sensitivity to Cyclosporine A", *J. Immunol.* 142: 4085 (1989).
Ito et al., "The Thiol Proteinase Inhibitors Improve the Abnormal Rapid Down-Regulation of Protein Kinase C and the Impaired Natural Killer Cell Activity in (Chediak–Higashi Syndrome) Beige Mouse", *Biochem. Biophy. Res. Comm.* 160:433–440 (Apr., 1989).
Ucker et al., "Activation–Driven T Cell Death", *J. Immunol.* 143: 3461 (1989).

Clerici et al., "Detection of Three Distinct Patterns of T Helper Cell Dysfunction in Asymptomatic, Human Immunodeficiency Virus–Seropositive Patients", *J. Clin. Invest.* 84: 1892 (1989).
Arends et al., "Apoptosis, The Role of the Endonuclease", *Am. J. Pathol.* 136:593 (1990).
Odaka et al., "T Cell Receptor–Mediated DNA Fragmentation and Cell Death in T Cell Hybridomas", *J. Immunol.* 144: 2096 (1990).
Shi et al., "Activation–induced Cell Death in T Cell Hybridomas is Due to Apoptosis", *J. Immunol.* 144: 3326 (1990) (erratum at 145: 3945).
Webb et al., "Extrathymic Tolerance of Mature T Cells: Clonal Elimination as a Consequence of Immunity", *Cell* 63:1249 (1990).
Zacharchuk et al., "Programmed T Lymphocyte Death", *J. Immunol.* 145: 4037 (1990).
Piedimonte et al., "Protease Activation During HIV Infection in a CD4–Positive Cell Line", *AIDS Res. Hum. Retrovir.* 6: 251–260 (1990).
Wang, "Developing Selective Inhibitors of Calpain", *Trends Pharmacol. Sci.* 11: 139–142 (1990).
Petteway et al., "The Chronically Infected Cell as a Target for the Treatment of HIV Infection and AIDS", *TiPS* 12: 28–34 (Jan. 1991).
Guy et al., "A Specific Inhibitor of Cystein Proteases Impairs a Vif–Dependent Modification of Human Immunodeficiency Virus Type 1 Env Protein", *J. Virol.* 65: 1325–1331 (Mar., 1991).
Croall et al., "Calcium–Activated Neutral Protease (Calpain) System: Structure, Function, and Regulation", *Physiol. Rev.* 71: 813–847 (1991).
Lee et al., "Inhibition of Proteolysis Protects Hippocampal Neurons from *Ischemia*", *Proc. Natl. Acad. Sci.* 88: 7233 (1991).
Sellins et al., "Cytotoxic T Lymphocytes Induce Different Types of DNA Damage in Target Cells of Different Origins", *J. Immunol.* 147:795 (1991).
Lucey et al., "Human Immunodeficiency Virus Infection in the US Air Force: Seroconversions, Clinical Staging, and Assessment of a T Helper Cell Functional Assay to Predict Change in CD4+ T Cell Counts", *J. Infect. Dis.* 164:631 (1991).

(List continued on next page.)

*Primary Examiner*—Christine M. Nucker
*Assistant Examiner*—Jeffrey S. Parkin
*Attorney, Agent, or Firm*—Townsend & Townsend & Crew LLP

[57] ABSTRACT

Calpain has been identified as a component of the biochemical pathway in programmed cell death. Calpain inhibitors are effective in preventing the progression to cell death and can restore cell function. T lymphocytes from HIV infected individuals undergo T cell receptor-triggered programmed cell death which can be treated by calpain inhibitors and immune function can be restored in affected cells. Methods for diagnosing cell populations or individuals susceptible to programmed cell death and for monitoring therapeutic effectiveness are provided.

5 Claims, 7 Drawing Sheets

OTHER PUBLICATIONS

Ameisen et al., "Cell Dysfunction and Depletion in AIDS: the Programmed Cell Death Hypothesis", *Immunol. Today* 12: 102–104 (1991).

Shenoy et al., "Inhibition of the Calpain–Mediated Proteolysis of Protein Kinase C Enhances Lytic Activity of Human NK Cells", *Cell. Immunol.* 138: 24–34 (1991).

Groux et al., "Activation–Induced Death by Apoptosis in CD4+ T Cells form Human Immunodeficiency Virus–Infected Asymptomatic Individuals", *J. Exp. Med.* 174: 331–340 (Feb., 1992).

Gadrielescu, "An Integrative Approach to the Proteolytic Control of the Cell–Mediated Cytotoxicity" *Roum. Arch. Microbiol. Immunol.* 51: 33 (Jan.–Jun., 1992).

Meyaard et al., "Programmed Death of T Cells in HIV–1 Infection," *Science* 257: 217–219 (Jul., 1992).

Bruno et al., "Inhibitors of Proteases Prevent Endonucleolysis Accompanying Apoptotic Death of HL–60 Leukemic Cells and Normal Thymocytes," *Leukemia* 6:1113–1120 (Nov., 1992).

Saido et al., "Positive Regulation of $\mu$–Calpain Action by Polyphosphoinositides" *J. Biol. Chem.* 267: 24585–24590 (Dec., 1992).

Ameisen, "Programmed Cell Death and AIDS: from Hypothesis to Experiment", *Immunol. Today* 13: 388–392 (1992).

Green et al., "Activation-induced Apoptosis in Lymphoid Systems", *Semin. Immunol.* 4: 379 (1992).

Gavrieli et al., "Identification of Programmed Cell Death in situ via Specific Labeling of Nuclear DNA Fragmentation", *J. Cell Biol.* 119: 493 (1992).

IN VITRO METHODS FOR ASSESSING THE SUSCEPTIBILITY OF HIV-1-INFECTED INDIVIDUALS TO CYSTEINE PROTEASE-MEDIATED ACTIVATION-INDUCED PROGRAMMED CELL DEATH

BACKGROUND OF THE INVENTION

Programmed Cell Death

Cell death has become recognized as a physiological process important in normal development, hormonal regulation of various tissues, and in regulation of the receptor repertoires of both T and B lymphocytes. A major unresolved problem is the lack of defined molecular pathways for such programmed cell death (PCD). The finding that a pattern of morphological changes is common to many examples of PCD led to the suggestion of a common mechanism, and the term apoptosis was defined to include both the morphological features and the mechanism common to such cell death (Kerr et al., Br. J. Cancer 26:239 (1972)). This concept was extended by the finding that nuclear DNA fragmentation correlates well with apoptotic morphology (Arends et al., Am. J. Pathol. 136:593 (1990)), and the scientific literature contains many examples of PCD accompanied by these features. The relationship between the DNA fragmentation and cell death pathways has not been elucidated. Furthermore, there are clear examples of PCD in the absence of apoptotic morphology or DNA fragmentation (Clarke, Anat. Embry. 181:195 (1990), Martin et al, J. Cell Biol. 106:829 (1988), and Ishigami et al., J. Immunol. 148:360 (1992)). New approaches to defining the molecular pathways of PCD and agents for inhibiting this process are clearly needed.

Lymphocyte-mediated cytotoxicity has been considered to be an example of apoptotic death since the target cells often (but not always) show DNA fragmentation (Sellins et al., J. Immunol. 147:795 (1991)) and apoptotic morphology (Webb et al., Cell 63:1249 (1990)). However, since in most cases there is no requirement for RNA or protein synthesis, this type of cell death has been considered to be a different category of apoptotic death (Goldstein et al., Immunol. Rev. 121:29 (1991)).

Infection by the human immunodeficiency viruses, HIV-1 and HIV-2, typically results in an early asymptomatic phase. During this period there is a selective loss of the ability of helper T ($T_H$) cells to proliferate in vitro in response to self major histocompatibility complex (MHC) class II restricted recall antigens while retaining the capacity to respond to mitogens such as phytohemagglutinin (PHA), and to alloreactive cells. Thus, some antigen-specific memory $T_H$ cells are present and, while failing to proliferate, they show at least partial activation after stimulation in vitro.

HIV infection affects $CD4^+$ $T_H$ cells in two different ways: qualitative $CD4^+$ $T_H$ cell functional defects can be detected very early, when only 1 in 10,000 to 1 in 1,000 $T_H$ cells are infected, followed several months or years later by quantitative decrease in the $T_H$ cell population that will lead to acquired immune deficiency syndrome (AIDS). It has been proposed that an inappropriate activation-induced T cell death, PCD, can account for both functional and numerical abnormalities of $T_H$ cells from HIV-infected patients, which leads to near complete collapse of a patient's immune system. Ameisen and Capron, Immunol. Today 12: 102–104 (1991); Ameisen, Immunol. Today 13: 388–392 (1992). According to this theory, HIV infection leads to an early priming of $T_H$ cells for a suicide process upon stimulation by antigen. In vivo, $T_H$ cell death after activation will progressively lead to a detectable decrease in the $T_H$ cell population. Thus, $T_H$ cells do not proliferate, but rather, the antigen induces $T_H$ cell death.

According to the programmed cell death model for HIV pathogenesis, the decline in immune reactivity and number of CD4+ lymphocytes associated with HIV infection is due to T cell receptor-induced programmed cell death (PCD) in CD4+ lymphocytes after contact with antigen. This abnormal response to antigen has been shown to be triggered by antigen in vitro after prior cross-linking of CD4 with either anti-CD4 antibody or with viral gp120 and anti-gp120.

Calpain

Calpain is a calcium-activated neutral protease located in the cytoplasm of many cell types. It is a member of the cysteine protease family, in common with several lysosomal cathepsins. There are two isoenzymes known as calpain I and II, which differ in their in vitro calcium requirements of activation, and in the amino acid sequence of the larger of the two peptide chains comprising the enzyme. Both calpain heavy chains and the common light chain have been sequenced after cDNA cloning (Suzuki, in Intracellular Ca-Dependent Proteolysis, Mellgren and Murachi, eds., CRC Press, Boca Raton, Fla., pp. 26–35 (1990)). All contain a calmodulin domain. Calpain activity regulation in situ is complex, being affected by the endogenous inhibitory protein calpastatin, proteolytic processing, interaction with membranes, and cytoplasmic calcium levels. Croall and Demartino, Physiol. Rev. 71: 813 (1991). Lymphocyte activation triggers a rapid rise in internal calcium, and lymphocytes have also been found to have the highest levels of calpains I and II of any cells measured (Murachi, Biochem. Int. 18:263 (1989)).

In spite of considerable study, the physiological role of calpain is not established (Croall and Demartino, supra). In platelets, calpain has been implicated in activation-induced vesiculation, apparently by cleavage of platelet cytoskeletal proteins (Fox et al., J. Biol. Chem. 266: 13289 (1991)).

A number of calpain inhibitors have been developed (Wang, Trends Pharmacol. Sci. 11: 139 (1990)). Some of these, e.g., E-64 and leupeptin, are effective on cysteine proteases generally, while others such as ALLnM have a selective effect on calpain. Although ALLnM is quite selective for calpain, it does react slowly with papain, another member of the cysteine protease family.

To date, calpain inhibitors have been of therapeutic interest principally in two clinical situations. One is in stroke, where there is evidence that increases in cytoplasmic calcium are responsible for nerve cell damage and death associated with ischemia. Since a specific calpain inhibitor blocked both neuronal death and brain spectrin proteolysis induced by ischemia, it has been suggested that calpain inhibitors may be useful as a treatment for stroke (Lee et al., Proc. Natl. Acad. Sci. 88: 7233 (1991)).

The second disease in which calpain inhibitors have been considered for use in therapy is muscular dystrophy. The most severe form of this disease, Duchenne muscular dystrophy, is a fatal genetic disease caused by a lack of expression of the cytoskeletal protein dystrophin. Muscle degeneration in this condition is accompanied by increases in intracellular calcium and Z-band loss, suggesting calpain activation. It was hypothesized that blocking calpain would prevent the subsequent steps in muscle cell damage and death, and calpain inhibitors were thus sought for therapy (Satoyoshi, *Intern. Med.* 31: 841 (1992)).

The cysteine protease inhibitor E-64 is a natural product, secreted by the fungus *Aspergillis japonica*. It is remarkably non-toxic to cells in vitro, and a number of experiments have been described in which it was given in vivo (Amamoto et al., *Biochem. Biophys. Res. Comm.* 118: 117 (1984); Hanada et al., in *Proteinase Inhibitors: Medical* and *Biological Aspects*, Katunuma, ed., Springer-Verlag, Tokyo, pp. 25–36(1983)). Since it inhibits lysosomal cathepsins B, H, and L, as well as calpain, it was considered as a potential agent which could block the muscle damage associated with muscular dystrophy. A series of E-64 derivatives has been prepared and their properties studied with respect to potential therapeutic use (Hanada et al., supra). Modification of E-64 to the compound E-64c, gave approximately equivalent potency to E-64. Both E-64 and E-64c are active when injected intraperitoneally but inactive when delivered orally. The ethyl ester of E-64c, termed EST (also known as E-64d, Loxistatin, or Ep-453) is readily absorbed from the gut and produce μmolar levels of E-64c in plasma several hours after administration (Hanada et al., supra).

What is needed in the art is a means to treat or prevent the decline in immune function that is typically associated with immunodeficiency diseases, particularly infection by HIV, that results in a collapse of the immune system and eventual death of the patient from secondary infections. Desirably, the treatment would be effective in the early asymptomatic phases of disease, when then progressive decline in the ability of $T_H$ cells to proliferate in response to antigens is initiated. Moreover, it would be extremely helpful to identify agents that are capable of restoring an immune system that has been devastated to near total loss by PCD. Quite surprisingly, the present invention fulfills these and other related needs.

SUMMARY OF THE INVENTION

The present invention provides pharmaceutical compositions useful in methods of inhibiting T lymphocyte deterioration and death caused by retroviral infection, such as caused by HIV. The compositions comprise pharmaceutically acceptable inhibitors of calpain, such as E-64 and derivatives thereof, leupeptin, ALLnM, and the like. Accordingly, the invention also provides methods of inhibiting symptomatic effects of a retroviral infection in an infected host. A calpain inhibitor is administered to the host in an amount effective to inhibit the deterioration of T lymphocyte function typically associated with HIV infection. The calpain inhibitor may be administered prophylactically to individuals infected but asymptomatic, or, in cases of well established infection and severely depleted T cell function the inhibitor may be administered to the host in multiple doses over a prolonged period of time. The calpain inhibitor may also be used in conjunction with other treatments designed to inhibit viral replication in a host. Typically the method of administration of the calpain inhibitor to the host will be oral or parenteral, e.g., intravenous or intramuscular. The calpain inhibitors and pharmaceutical compositions thereof can also be used in extracorporeal treatment of a host's cells, and in methods of inhibiting retrovirus induced cell death in cell cultures. Furthermore, the invention also provides means to screen for additional compounds which potentiate the cell death-inhibiting effect of a calpain inhibitor of the invention.

DESCRIPTION OF THE SPECIFIC EMBODIMENTS

Figure 1:
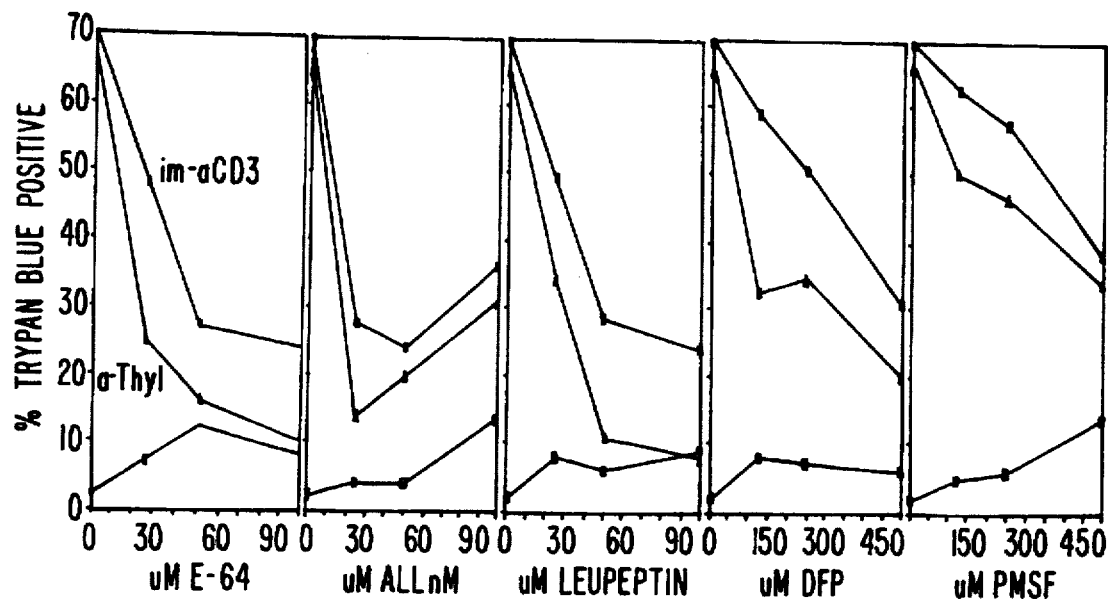
FIG. 1 illustrates the effect of selected protease inhibitors on αCD3 and anti-Thy-1 induced programmed cell death in 2B4 cells. 2B4 cells were put into wells containing immobilized anti-CD3 (filled rectangles), anti-Thy-1 Mab G7 at 5 μg/ml (triangles), or control wells (open rectangles), and protease inhibitors were added at the initiation of culture, to the final concentration indicated. Cell viability was assessed with trypan blue after 16 hrs of culture.

The present invention provides pharmaceutical compositions useful in methods for inhibiting or reversing calpain-mediated programmed cell death (PCD). It has been discovered as part of the present invention that calpain, a cytoplasmic calcium-dependent cysteine protease, is directly or indirectly part of a biochemical pathway that leads to cell death. Calpain is particularly involved in the cell death pathway that is triggered by the T cell receptor (TcR). Accordingly, inhibitors of calpain are able to inhibit the PCD pathway and either restore cellular function or prevent its further deterioration. As there are many cysteine proteases, inhibitors which are specific for calpain are particularly preferred in the present invention.

As part of the present invention it has been shown that lymphocytes from asymptomatic individuals infected with HIV, when cultured with agents which crosslink the TcR, undergo death accompanied by apoptotic morphology and DNA fragmentation. Such apoptotic death is usually not observed in lymphocytes obtained from uninfected individuals. These findings indicate that HIV infection causes uninfected T cells in the individual to respond to antigen by dying, rather than undergoing activation and proliferation. Treatment of the lymphocytes with calpain inhibitors reverses the TcR-induced PCD. Moreover, calpain inhibitors can restore T cell responses of some asymptomatic HIV-infected individuals to a variety of antigens for which an individual's response had been severely depressed. The results described herein explain at least in part the observation that in HIV infected individuals, CD4+ blood lymphocytes decline in number and in functional activity to many antigens when only a small fraction (generally less than 0.1%) of the CD4+ lymphocytes are infected with the virus. Thus, HIV may actually prime an individual's T cells, including CD8+ cells, to undergo PCD when the cells encounter their respective antigen.

As used herein, by "programmed cell death," or "activation-induced cell death," or "apoptosis" is meant an active cell death mechanism that results in a characteristic DNA fragmentation pattern in multiples of about a 190–200 base pair unit, as detected on agarose gels, and a condensation of nuclear chromatin. This process renders the cells unresponsive to antigen stimulation, although the PCD phenomenon is not limited solely to lymphocytes.

The PCD which is amenable to treatment by the methods of the present invention is mediated at least in part by calpain. The use of calpain inhibitors is not limited, however, to treatment of viral-induced calpain-mediated PCD in lymphocytes, as the methods described herein can treat a variety of other pathological and undesirable conditions which are manifested at the cellular level by calpain-mediated PCD. For example, HIV-induced neurological damage may be treated with calpain inhibitors. Also, calpain-mediated PCD is involved in TcR-triggered death in murine T cell hybridomas, such as 2B4 exemplified below. PCD has been implicated in a wide variety of immunological regulatory and dysfunctional processes. To identify calpain-mediated PCD, mammalian cells of interest suspected of undergoing PCD are initially confirmed to be susceptible to PCD. The PCD process is generally associated with a typical cellular morphology, such as extensive peripheral chromatin condensation, dilation of the endoplasmic reticulum, and preservation of mitochondrial structures, and degradation of the DNA into discrete fragments of about 190–200 base pairs. Wylie et al., *Int. Rev. Cytol.* 68: 251 (1980) and Wylie et al., *J. Pathol.* 142: 67 (1984), both incorporated herein by reference. To determine whether the PCD process in susceptible cells involves calpain in the cell death pathway, the cells are treated with a calpain-specific inhibitor. The results are compared to an untreated cell sample, and if cells treated with the calpain inhibitor demonstrate a restoration, inhibition or reversal of PCD or other conveniently monitored functional attribute(s), such as proliferative ability in response to stimulation, the PCD is determined to be calpain-mediated and susceptible to treatment according to the present invention.

The present methods may also be effective in treating autoimmune or autoimmune-associated diseases, particularly those which are associated with immunodeficiencies. For example, there is evidence that AIDS involves an autoimmune-mediated destruction of $T_H$ subsets. See, e.g., Shearer, *Mt. Sinai J. Med.* 53: 609–615 (1986), and Andrieu et al., *AIDS Res.* 2: 163–174 (1986). Other autoimmune diseases which may be treated according to the present methods may be identified according to the methods described herein for assessing the involvement of PCD and the ability of protease inhibitors, and particularly calpain inhibitors, to reverse the PCD associated with the disease.

A number of calpain inhibitors are useful in the methods of the present invention. Calpain inhibitors have been described previously. Some of these calpain inhibitors are specific for calpain while others also inhibit a broader array of cysteine proteases. For example, because the sulphydryl group of Cys108 must be in its reduced form for the enzyme to be active, it is susceptible to thiol-reactive agents such as iodoacetic acid and N-ethyl-maleimide, but these agents, which are widely available, inhibit all cysteine proteases and many other cellular proteins See, e.g., Pontremoli and Melloni, *Ann. Rev. Biochem.* 55: 455–481 (1986); Suzuki, *Trends Biochem. Sci.* 12: 103–105 (1987); and Murachi, *Biochem. Int.* 18: 263–294 (1989), which are each incorporated herein by reference. $Ca^{+2}$ chelators, such as EDTA, EGTA, and BAPTA have been used to block calpain activity, but they also block other $Ca^{+2}$ dependent processes. The similarity between the $Ca^{+2}$ binding domains of calpain and calmodulin permits calmodulin antagonists, such as melittin, calmidazolium trifluoperezine and W7 to also inhibit calpain, but the $IC_{50}$s for these agents are often 10–600 times higher for calpain than for calmodulin. Brumley and Wallace, *Biochem. Biophys. Res. Commun.* 159: 1297–1303 (1989), incorporated herein by reference.

One of the more widely used calpain inhibitors is leupeptin, a microbial peptide aldehyde (R-Leu-Leu-Arg-H). However, leupeptin also suffers from a lack of selectivity and further acts as a serine protease inhibitor. A more hydrophobic aldehyde peptide, cBz-Val-Phe-H (obtainable from Sigma, St. Louis, Mo.) may provide greater membrane permeability. Mendi et al., *Bioshem. Biophys. Res. Comm.* 157: 1117–1123 (1988). E-64, which is isolated from *Aspergillus japonicus*, is a member of the epoxysuccinyl peptide inhibitors of calpain. Parkes et al., *Biochem. J.* 230: 509–516 (1989), incorporated herein by reference In the presence of $Ca^{2+}$, E-64 irreversibly inhibits calpain and other cysteine proteases. The E-64 derivative, E-64c, is useful in the invention, and the ethyl ester derivative of E-64c, designated E-64d, is membrane permeable and is also particularly preferred for oral administration in the present invention. See also, Shoji-Kasai et al., *Proc. Natl. Acad. Sci.* 85: 146–150 (1988), which is incorporated herein by reference.

To minimize cross-reactivity and possible adverse toxicities, it is desirable to use inhibitors that are even more highly selective for calpain and which retain the ability to permeate mammalian cell membranes. For example, another peptide aldehyde which is membrane permeable is calpeptin (cBz-Leu-nLeu-H). Calpeptin has improved selectivity for calpain over papain, and has been used to pretreat intact platelets and to inhibit calpain-mediated proteolysis of platelet proteins. Tsujinaka et al., *Biochem. Biophys. Res. Comm.* 153: 1201–1208 (1988), incorporated herein by reference. The peptide aldehydes Ac-Leu-Leu-nLeu-H and Ac-Leu-Leu-nMet-H also have selectivity for calpain over papain. Yet another selective calpain inhibitor is Leu-Leu-Phe-$CH_2$-Cl, which is a peptidyl chloromethyl ketone protease inhibitor which alkylates the sulfhydryl group ion the active site Cys in calpain. Sasaki et al., *J. Biochem.* 99: 173–179 (1986), incorporated herein by reference.

A particularly useful calpain inhibitor is calpastatin and derivatives therof. Calpastatin is a endogenous calpain inhibitor whose binding to calpain is $Ca^{2+}$ dependent and is reversed upon removal of $Ca^{2+}$. Once calpain is bound to calpastatin, calpain is incapable of autolysis of proteolysis of substrates. Calpastatin has not been reported to inhibit other proteases. Dayton et al., *Biochemistry* 15: 2150–2167 (1976). Synthetic oligopeptides, including one of 27 amino acids, which corresponds to a conserved region of calpastatin, have been prepared and found to regulate calpain activity. See, e.g., Maki et al., *J. Biol. Chem.* 264: 18866–18869 (1989) and EP publication 395,309, incorporated herein by reference. Shorter calpain binding peptides can be identified from the sequence of calpastatin, or may be identified in any of a variety of selective screening procedures. See generally, WO 91/17271, WO 91/19818, and WO 92/02536 and WO 92/15702, which are incorporated herein by reference. The smaller peptides may also be designed to mimic the binding or functional domains of the native protein. The oligopeptides so identified can be synthesized by standard techniques in solution or on a solid support in accordance with conventional techniques. See, e.g., Stewart and Young, *Solid Phase Polypeptide Synthesis*, 2d ed., Pierce Chemical Company (1984), incorporated herein by reference.

The compositions may be administered to persons or mammals suffering from or predisposed to suffer from abnormal lymphocyte PDC. The calpain inhibitors can bind the calpain active site and inhibit protease activity directly. The inhibition of calpain in turn inhibits one or more biochemical pathways which lead to cell deterioration and loss of functionality, eventually leading to cell death even though the afflicted cell may not be infected by the virus which activates directly or indirectly the cell death pathway. By inhibiting this pathway, not only is cell death prevented, but functionality, such as immunoproliferative capacity, may be restored to the cell. Thus, while the replication or spread of the virus may be only impeded by this treatment, the patient retains or regains a responsive immune system and thus can better respond to other antigenic challenges. As infections secondary to HIV are a major cause of death of AIDS patients, the treatment afforded by the present invention presents a major step toward eliminating the potentially devastating effects of this disease.

The compositions also find use for pre- or post-exposure prophylaxis, e.g., HIV prophylaxis following dirty needle injuries to health care workers or routinely accompanying blood transfusions or to persons in danger of becoming exposed to infected body or culture fluids. Retroviruses may not become latent, but merely replicate by a slow and regulated process in the initial phases of infection.

The pharmaceutical compositions are intended for parenteral, topical, oral, or local administration for prophylactic and/or therapeutic treatment. Preferably, the pharmaceutical compositions are administered orally or parenterally, i.e., intravenously, subcutaneously, or intramuscularly. Thus, this invention provides methods which employ compositions for oral or parenteral administration which comprise a solution of a calpain inhibitor dissolved in a pharmaceutically acceptable carrier, preferably an aqueous carrier. A variety of aqueous carriers may be used, e.g., water, buffered water, 0.4% saline, 0.3% glycine, and the like, including proteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such an pH adjusting and buffering agents, tonicity adjusting agents and the like, for example, sodium acetate, sodium lactate, sodium chloride, potassium chloride, calcium chloride, etc.

The concentration of the calpain inhibitor in these formulations can vary widely, i.e., from less than about 0.5%, usually at or at least about 1% to as much as 15 or 20% by weight and will be selected primarily by fluid volumes, viscosities, etc., in accordance with the particular mode of administration selected. Actual methods for preparing orally and parenterally administrable compounds will be known or apparent to those skilled in the art and are described in detail in, for example, Remington's Pharmaceutical Science, 17th ed., Mack Publishing Company, Easton, PA (1985), which is incorporated herein by reference.

Determination of an effective amount of calpain inhibitor to inhibit PCD in a patient's lymphocytes can be determined through standard empirical methods which are well known in the art. Reversal of impairment of immune function, e.g., restoration of lymphoproliferative response to recall antigen (e.g., influenza), alloantigens or mitogens such as PWM or PHA, and thus efficacy of the subject compositions, can be monitored with a variety of well known in vitro T cell proliferative response procedures.

Compositions of the invention are administered to a host already suffering from an infection, as described above, in an amount sufficient to prevent or at least partially arrest the development of PCD and the ensuing immunodeficiency disease and its complications. An amount adequate to accomplish this is defined as "therapeutically effective dose." Amounts effective for this use will depend on the severity of the infection or disease and the weight and general state of the patient being treated, but generally range from about 3 mg/kg to about 300 mg/kg host body weight of calpain inhibitor per day, with dosages of from about 10 mg/kg to about 30 mg/kg of calpain inhibitor per day being more commonly used. Maintenance dosages over a prolonged period of time may be adjusted as necessary. The period of administration will generally be sufficient to restore the immune system of the host, such that effective immune responses can be mounted against a variety of antigens, most desirably the HIV virus in the case of individuals infected with HIV. If an individual's restored immune system is not able to eliminate the disease, maintenance dosages over a prolonged period may be necessary. Also, it must be kept in mind that the materials of the present invention may be employed in life-threatening or potentially life threatening situations. In such cases, it is possible and may be felt desirable by the treating physician to administer substantial excesses of these compositions. For veterinary uses higher levels may be administered as necessary while avoiding, however, undesirable toxicities.

In prophylactic applications, compositions containing the calpain inhibitor, e.g., E64-d or ALLnM, are administered to a patient susceptible to or otherwise at risk of calpain mediated lymphocyte PCD to enhance the patient's own lymphocyte capabilities. Such an amount is defined to be a "prophylactically effective dose." In this use, the precise amounts again depend on the patient's state of health and weight, but generally range from about 3 mg/kg to about 300 mg/kg body weight, more commonly from about 10 mg/kg to about 30 mg/kg of body weight.

Single or multiple administrations of the compositions can be carried out with the dose levels and pattern being selected by the treating physician. In any event, the pharmaceutical formulations should provide a quantity of calpain inhibitor sufficient to effectively inhibit the calpain-mediated PCD in the host's cells.

The methods of the invention can be employed for ex vivo therapy. By ex vivo or extracorporeal therapy is meant that therapeutic manipulations are performed on cells outside the body. For example, lymphocytes or other target cells may be removed from a patient and treated with high doses of the calpain inhibitors, providing a concentration of inhibitor in the cell far in excess of levels which could be accomplished or tolerated by a patient. Following treatment, the cells are returned to the host to treat the PCD-related disease. Treated cells can also be propagated in vitro and returned to the patient after reaching a predetermined cell density. See generally, U.S. Pat. No. 4,690,915 to Rosenberg, which is incorporated herein by reference.

For use in the present methods a calpain inhibitors can be combined with one or more other calpain inhibitor to provide enhanced therapeutic activity. The calpain inhibitors can also be combined with other pharmaceutical compositions for a variety of therapeutic uses. For example, in the treatment of HIV infection, the pharmaceutical compositions of the present invention may be administered alone or as adjunct therapy with, e.g., AZT or ddI, or combinations thereof, such as AZT, ddI, and pyridinone. When administered as adjunct therapy, the calpain inhibitor may be administered in conjunction with the other treatment modalities, or separately at different intervals.

To enhance delivery of the calpain inhibitor to PCD susceptible cells, e.g., T lymphocytes, the calpain inhibitors can be targeted to the cells by a variety of means. For example, the inhibitors can be conjugated to antibodies or binding fragments thereof which bind antigens such as CD3 or CD4 expressed on the surface of lymphocytes and T helper cells, respectively. The calpain inhibitors can also be incorporated into other targeting vehicles, such as liposomes which comprise an antibody or binding fragment to direct the liposomes to the infected cells. The preparation of immunoliposomes is described in, e.g., U.S. Pat. No. 4,957, 735 which is incorporated herein by reference.

Calpain inhibitors also find use in vitro in the present invention to inhibition PCD of cultured cells, such as certain hybridoma or other lymphocyte lines which are susceptible to PCD upon TcR crosslinking, and thus can be treated with calpain inhibitors to inhibit the PCD.

In addition, by determining whether the cells of a patient are susceptible to PCD, and determining whether the PCD in the patient's cells is susceptible to inhibition or reversal by calpain inhibitors, appropriate therapy can be instituted or the effect of other treatment modalities, such as anti-HIV regimens, can be determined. Thus, a diagnostic method for assessing the efficacy of, e.g., anti-HIV therapy is also provided by the present invention. Detecting changes in vitro in the level of PCD susceptibility, or immune function such as restoration of response to recall antigens (e.g., influenza), to alloantigens, or to mitogens such as PWM or PHA, provides an indication of in vivo PCD activity and the molecular pathway responsible for immunodeficiency.

To monitor changes in the level of PCD in a cell population, control values of PCD may be determined from cells from the general population or from the patient prior to commencement of therapy. Since PCD may vary considerably among patients, determination of each patient's pretreatment PCD levels is preferred. The level of PCD or in vitro immune function in cells, e.g., lymphocytes in the case of HIV-infected individuals, is then determined during therapy. This level is compared to the level of the PCD or immune function in cells not exposed to therapy. Effectiveness of therapy is indicated by an increased level in the measured immune function during or post-therapy.

The following examples are offered by way of illustration, not by way of limitation.

EXAMPLE I

Inhibition of Programmed Cell Death in Lymphocytes

The murine CD4+ T cell hybridoma 2B4 was chosen for these experiments in part because it undergoes PCD in response to TcR crosslinking (Green et al., Semin. Immunol. 4: 379 (1992).

Effect of Selected Protease Inhibitors on TcR-Triggered PCD

To determine whether intracellular protease activation was part of a molecular pathway for PCD, the effects of a variety of protease inhibitors were examined on several PCD systems. The murine T cell hybridoma 2B4 is a well-defined system which has been shown to undergo PCD in response to T cell receptor cross-linking (Ucker et al., J. Immunol. 143: 3461 (1989); Mercep et al., J. Immunol. 142: 4085 (1989); and Zacharchuk et al., J. Immunol. 145:4037 (1990)). Similar TcR induced death has been reported with other murine T cell hybridomas (Okada et al., J. Immunol.

144: 2096 (1990); and Shi et al., *J. Immunol.* 144: 3326 (1990) (erratum at 145: 3945)).

The 2B4 hybridoma cells used in this study produce an antibody which binds to cytochrome C (Ashwell et al., *J. Exp. Med.* 165: 173 (1987)), and were obtained from Drs. A. Weissman and C. Cenciarelli of the National Cancer Institute, Bethesda, Md. They were cultured in RPMI 1640 with 10% FCS, as described. PCD was induced by immobilized 2C11 anti-CD3 antibody (Leo et al., *Proc. Natl. Acad. Sci.* 84:1374 (1987) or H57 anti-TcR$_{\alpha\beta}$antibody (Lee et al., *J. Biol. Chem.* 267: 8437 (1987)), prepared by precoating flat-bottom microtiter wells with 20 μg/ml purified MAb in 0.1M NaHCO$_3$ overnight at 5°. Cell number per well varied with the test used: $1\times10^4$ for $^{51}$Cr assay, $1\times10^5$ for trypan, propidium and IL-2 secretion, and $4\times10^5$ for growth inhibition and dye reduction.

A number of protease inhibitors which could inhibit candidate activatable intracellular proteases were tested for toxicity on 2B4 cells, and those which were non-toxic at what were judged to be effective concentrations were then tested for their ability to reverse PCD induced by overnight culture on immobilized MAb against the TcR complex, or by the soluble anti-Thy-1 MAb G7. Five such inhibitors showed a consistent ability to reverse this PCD. These include three calpain inhibitors: the epoxysuccinyl compound E-64, and the peptide aldehyde analogues leupeptin and ALLnM, and the classical serine protease inhibitors DFP and PMSF. FIG. 1 shows an experiment in which trypan blue was used to assess cell death after 16 hours of culture; all five protease inhibitors showed a clear dose-related ability to reverse death induced by both immobilized α-CD3 and α-Thy-1, at inhibitor concentrations having minimal effect on the viability of unstimulated control cells. The most potent inhibition of both anti-Thy-1 and anti-CD3 induced cell death was the calpain selective inhibitor ALLnM, which showed maximal inhibition of death in the 25–50 μM range; however, higher concentrations of this compound were clearly toxic, as seen by their increase in trypan blue staining of unstimulated 2B4 cells. The cysteine protease inhibitors E-64 and leupeptin also showed a potent ability to reverse PCD, giving maximal effects at 50–100 μM. In contrast, the serine protease inhibitors DFP and PMSF also revered this death, but with concentrations greater than 500 μM necessary to achieve a maximal effect. All these protease inhibitors gave greater inhibition of α-Thy-1 induced death than α-CD3 induced death. Similar results were obtained using mitochondrial dye reduction to assess viability after the overnight culture.

Protease Inhibitors Do Not Block Other TcR-Triggered Functions

To test for the possibility that the protease inhibitors block steps in the signal transduction pathway of the TcR (although not previously reported with the inhibitors used), IL-2 secretion was measured by assaying the culture supernatants after an overnight culture.

For the IL-2 assay, culture supernatants were harvested and diluted 2-fold with fresh medium into 96-well plates. CTLL cells ($2\times10^4$/well) were added and cultured 24 hours, after which 0.5 μCi $^3$H-thymidine was added to each well followed by another 24 hours of culture. The plates were harvested on an automated filter harvester and counted. r-Human-IL-2 (Cetus) was similarly diluted and used as a standard.

Figure 2:
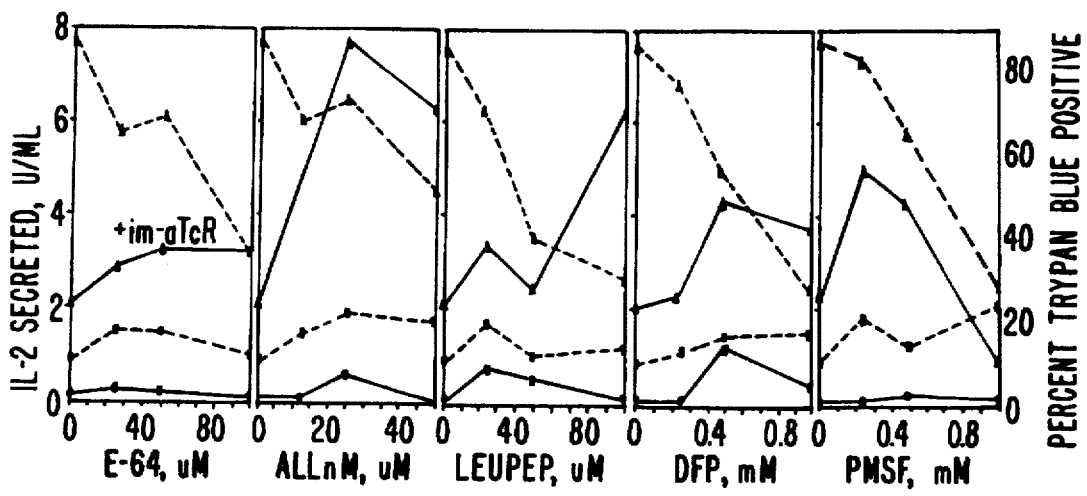
FIG. 2 depicts the effect of protease inhibitors on TcR induced PCD and IL-2 secretion in 2B4 cells. Cultures were established in wells having immobilized anti-TcRβ (triangles) or without stimulation (rectangles). At the end of 16 hours, supernatants were harvested for assay of IL-2 (solid lines) and the cell viability was assessed with trypan blue (dashed lines).

As can be seen in FIG. 2, IL-2 secretion triggered by immobilized antibody to TcR β was generally increased by the protease inhibitors which had shown reversal of cell death. In some cases as much as a 3-fold enhancement was seen in this experiment (with ALLnM), and in other experiments as much as a 7-fold enhancement was observed (also with ALLnM). Since the TcR stimulus triggers both death and IL-2 secretion, an enhancement of the latter may be expected if the death pathway is selectively inhibited.

Figure 3:
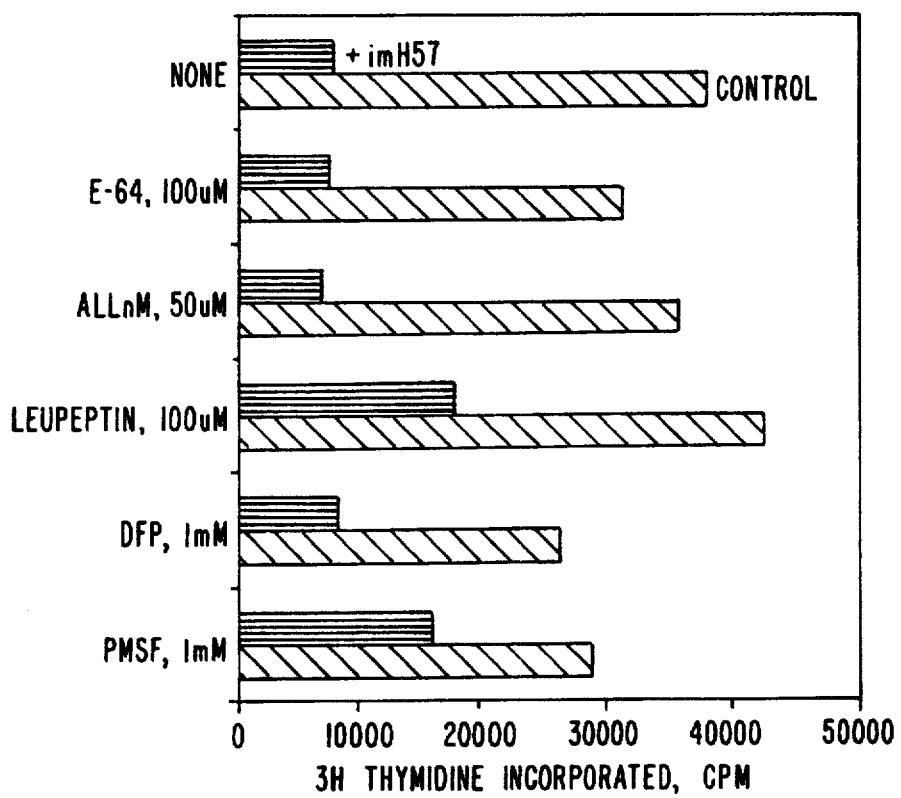
FIG. 3 shows the effect of protease inhibitors on T cell receptor-mediated growth inhibition, where 2B4 cells (20,000 per well) were cultured on wells coated with immobilized H57 (solid bars) or control wells (striped bars) for 6 hours, after which each well was pulsed with 1 μc of $^3$H-thymidine for 1.5 hours prior to harvest.

It has been previously shown that 2B4 cells respond to TcR cross-linking by growth inhibition as measured by the early inhibition of $^3$H-thymidine incorporation. This response is distinct from cell death in that it is not calcium dependent or inhibited by cyclosporin A (Mercep et al.,. *J. Immunol.* 142:4085 (1989)). FIG. 3 shows that the selected protease inhibitors generally have a minimal or negligible effect on this growth inhibition response. The experiment shown was pulsed with thymidine after 6 hours of incubation with antibodies. Other experiments in which the cultures were pulsed after 3 hours gave similar results. There is some (0–30%) reduction in the level of control thymidine incorporation by several of the protease inhibitors, which complicates the interpretation of these experiments. Leupeptin reproducibly showed a partial restoration (20–35%) of the growth inhibition as shown in FIG. 3, and PMSF showed a variable degree of partial restoration of thymidine incorporation. The partial restoration by PMSF seen in this experiment was not reproduced in other experiments. The other inhibitors showed little or no restoration of the responses depressed by TcR cross-linking. Thus, the growth inhibition response is largely unaffected by protease inhibitors, in contrast to the cell death response. These data thus support the interpretation that growth inhibition, measured by thymidine incorporation within 6 hours of TcR cross-linking, involves an effector pathway which diverges from that responsible for cell death.

Protease inhibitors Do Not Block Cell Death By Other Agents

Figure 4:
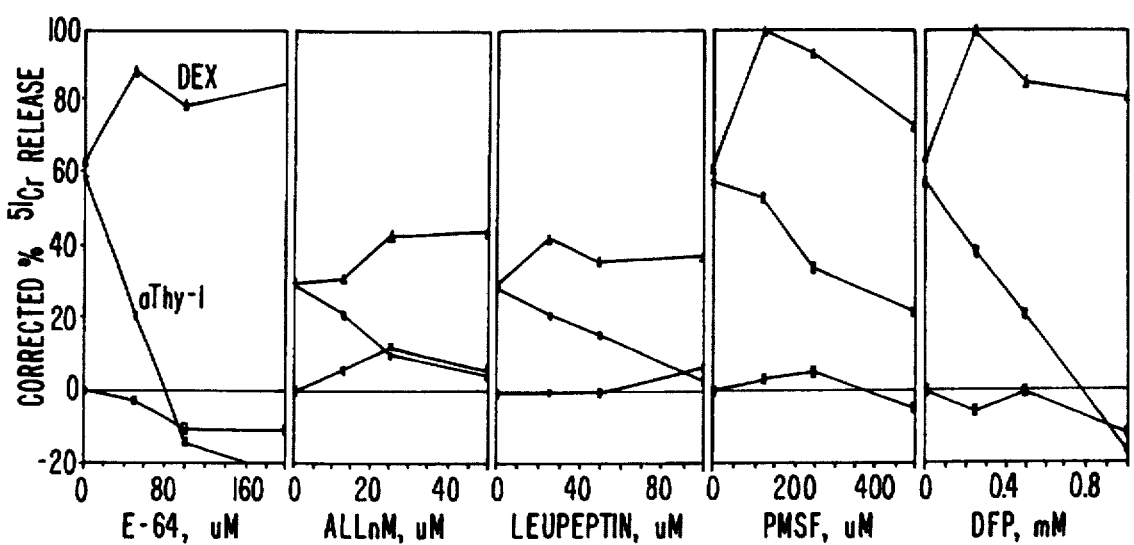
FIG. 4 depicts the effect of protease inhibitors on 2B4 PCD induced by TcR, Thy-1, or corticosteroid (dexamethasone). $^{51}$Cr-labelled 2B4 cells were cultured overnight with the indicated stimuli, and the $^{51}$Cr label released into the supernatant measured. Representative panels from two separate experiments are shown. The spontaneous releases were 35% in the experiment with ALLnM and Leupeptin which utilized anti-TcR, and 54% in the other.

In addition to antibodies against the TcR complex and Thy-1, corticosteroids have been shown to induce programmed cell death in 2B4 cells (Zacharchuk et al., *J. Immunol.* 145: 4037 (1990)). FIG. 4 shows $^{51}$Cr release experiments to test whether the selected protease inhibitors blocked PCD induced by dexamethasone, a synthetic corticosteroid. The $^{51}$Cr release assay was performed using 2B4 cells in 5 ml culture medium, labeled by addition of 300 μg Na$_2$$^{51}$CrO7 (Amersham) for 2 hours in the CO$_2$ incubator. The cells were then harvested and washed prior to use in the PCD assay. Spontaneous release for the 12–16 hour assays used were 30–45%.

While the protease inhibitors showed the expected reversal of PCD triggered by the stimuli described above, death induced by dexamethasone was modestly but clearly enhanced by all five of the protease inhibitors in a dose-dependent response (FIG. 4). $^5$Cr release was not induced by the protease inhibitors alone at the concentrations used. The enhancement of corticosteroid induced death was seen over a wide range of steroid concentrations as shown by their effects in the two experiments depicted in FIG. 4. Thus the two antagonistic pathways giving PCD in 2B4 are influenced in opposite directions by the protease inhibitors.

The effect of protease inhibitors was examined on a number of other cytotoxic agents and conditions applied to 2B4 cells during an overnight culture. In these experiments, the 2B4 cells were pretreated with protease inhibitors for 30 min. prior to culture to allow them to work where the toxic effects might be more rapid than the PCD studied previously. A negligible effect with all the inhibitors tested was observed in some cases, such as with the membrane pore-forming agent Staphylococcal α-toxin (Bhakdi et al., *Microbiol. Rev.* 55: 733 (1991) (shown in FIG. 5), the lysosomotropic detergent dodecyl imidazole (Wilson et al., *J. Cell. Biol.* 104: 1223 (1987)), hypotonic conditions (50% water).

Figure 5:
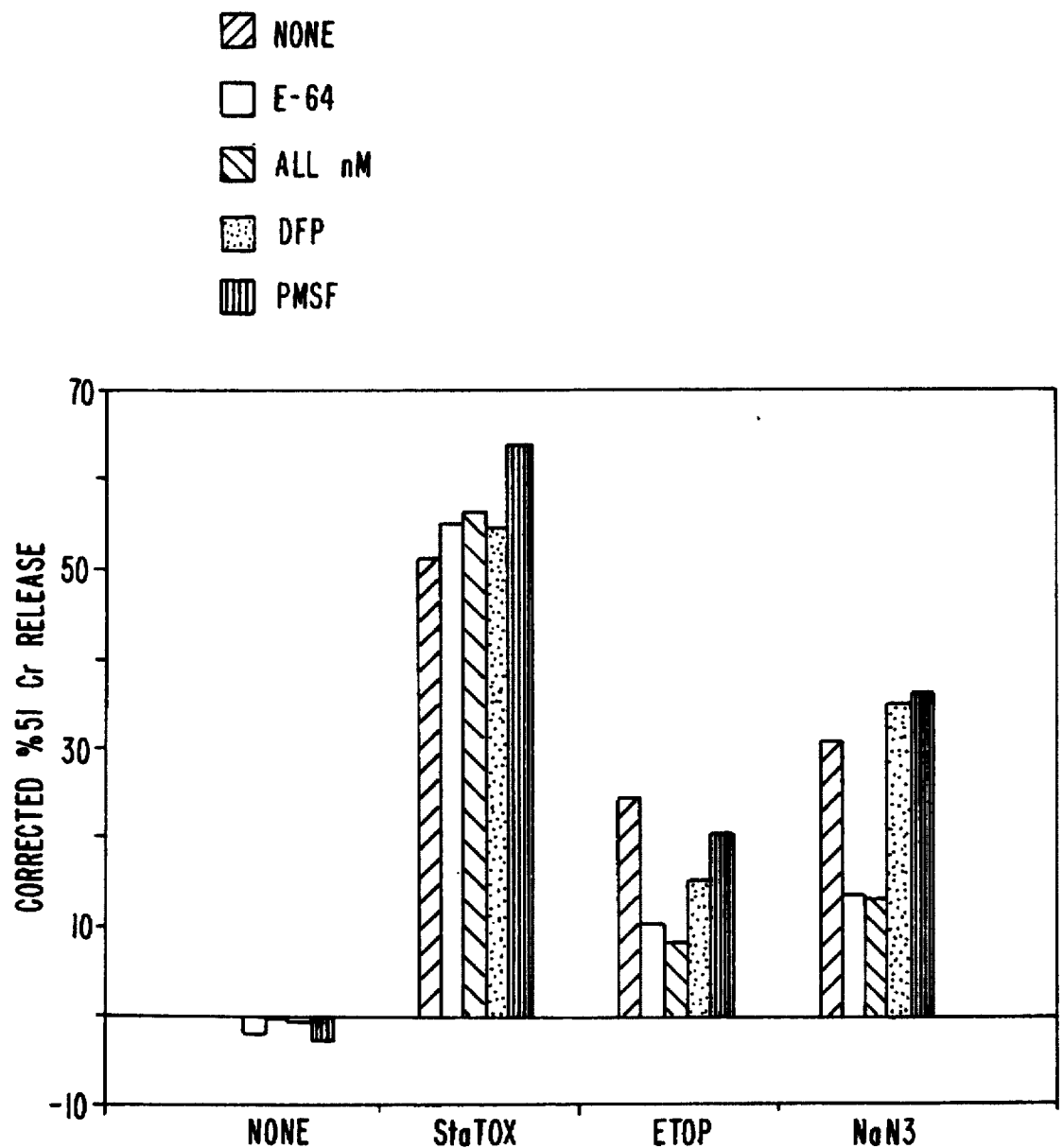
FIG. 5 illustrates the effect of protease inhibitors on 2B4 cell death induced by various agents. Overnight 2B4 cultures were established, with the following final concentrations of protease inhibitors, precultured with the cells for 30 minutes prior to adding the toxic agent. The cultures were then cultured for 13 hours and the $^{51}$Cr label released into the supernatant measured. The spontaneous release in this experiment was 26%. The inhibitor final concentrations used were: E-64, 100 μM; ALLnM, 50 μM; DFP, 1 mM; PMSF, 1 mM. Final concentrations of cytotoxic agents were: Staphylococcal α-toxin, 5 μg/ml; etoposide, 5 μg/ml; NaN$_3$, 1 mg/ml.

FIG. 5 also shows that cell death induced by other toxic agents can be either enhanced or suppressed by protease inhibitors. Death by the topoisomerase II inhibitor and chemotherapeutic agent etoposide (Liu, *Ann. Rev. Biochem.* 58: 351 (1989)) was generally blocked by the protease inhibitors, albeit not as completely as that by TcR crosslinking. Cell death elicited by sodium azide was blocked by cysteine but not serine protease inhibitors (FIG. 5). Protease inhibitors block TcR-mediated apoptotic nuclear morphology changes and DNA fragmentation.

Figure 6A:
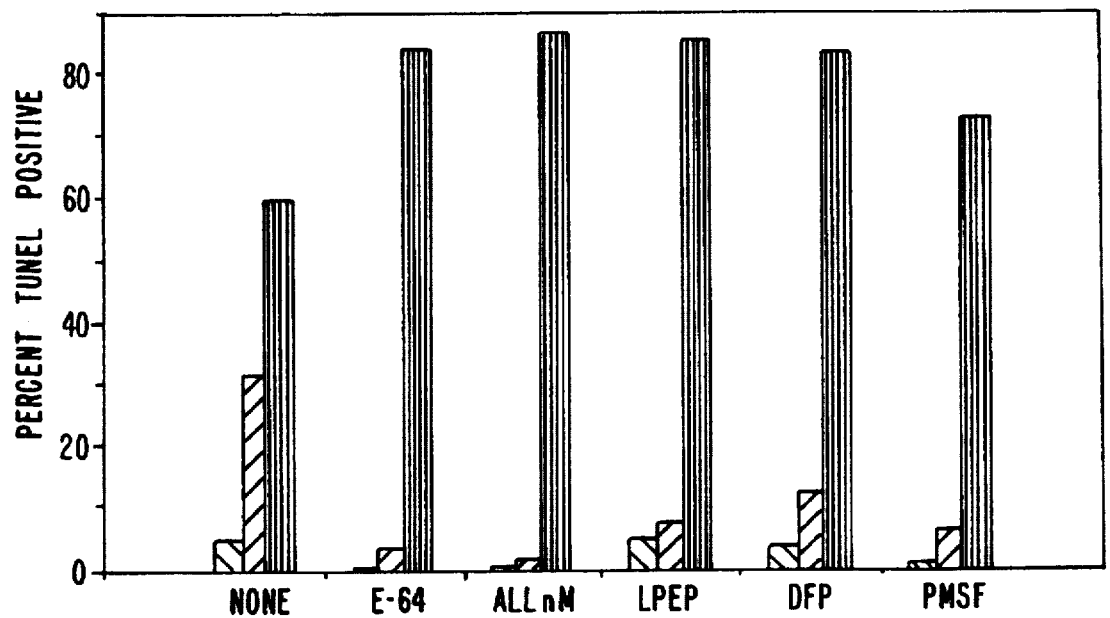
FIG. 6 depicts the TcR-induced apoptotic nuclear morphology changes and DNA fragmentation blocked by protease inhibitors. 2B4 cells were cultured 17 hours alone (diagonal stripped bars), on immobilized a-TcR$_{\alpha\beta}$(filled bars) or with 1×10$^8$M dexamethasone (hatched bars), in the presence of the protease inhibitors indicated. Cells were analyzed for DNA fragmentation by the TUNEL technique, or for nuclear morphology by examination of Hoechst 33342 stained cells.
Figure 6B:
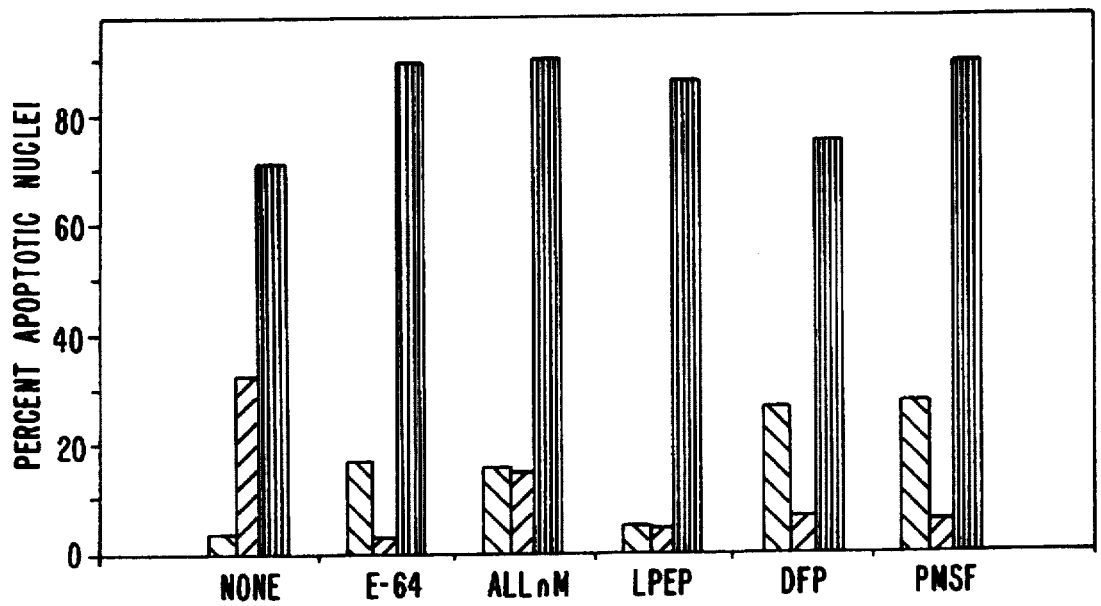

FIG. 6 shows an experiment which tested the effect of protease inhibitors on the apoptotic changes associated with 2B4 PCD. DNA fragmentation was assessed by the TUNEL technique, which measures DNA fragmentation in situ using terminal transferase and biotinylated dUTP (Gavrieli et al., *J. Cell Biol.* 119: 493 (1992)), and nuclear morphology was assessed by fluorescence microscopy using the DNA staining dye Hoechst 33342 (obtained from Molecular Probes, Eugene, OR).

The results show that both the TcR-induced DNA fragmentation and nuclear morphology changes in 2B4 were reversed by the protease inhibitors in parallel with their inhibition of cell death measured by membrane permeability. Furthermore, the increased death seen with dexamethasone in the presence of protease inhibitors is also clearly apoptotic by both criteria. Both determinations of apoptotic changes are parallel to each other and to death measured by membrane integrity measurements.

The nuclear morphology of 2B4 cells treated with both etoposide and sodium azide was clearly apoptotic, while that of 2B4 cells treated with hypotonic shock, staphylococcal α-toxin and dodecyl imidazole were predominantly non-apoptotic. Thus, the protease inhibitors tended to have either positive or negative influences on apoptotic 2B4 deaths, and little or no effect on non-apoptotic cell deaths.

EXAMPLE II

Reversal of PCD in Lymphocytes of HIV+ Individuals

This Example describes the use of calpain inhibitors to reverse TcR mediated PCD in HIV infected asymptomatic individuals and shows that severely depressed T cell responses can be restored in some of the infected individuals.

Figure 7A:
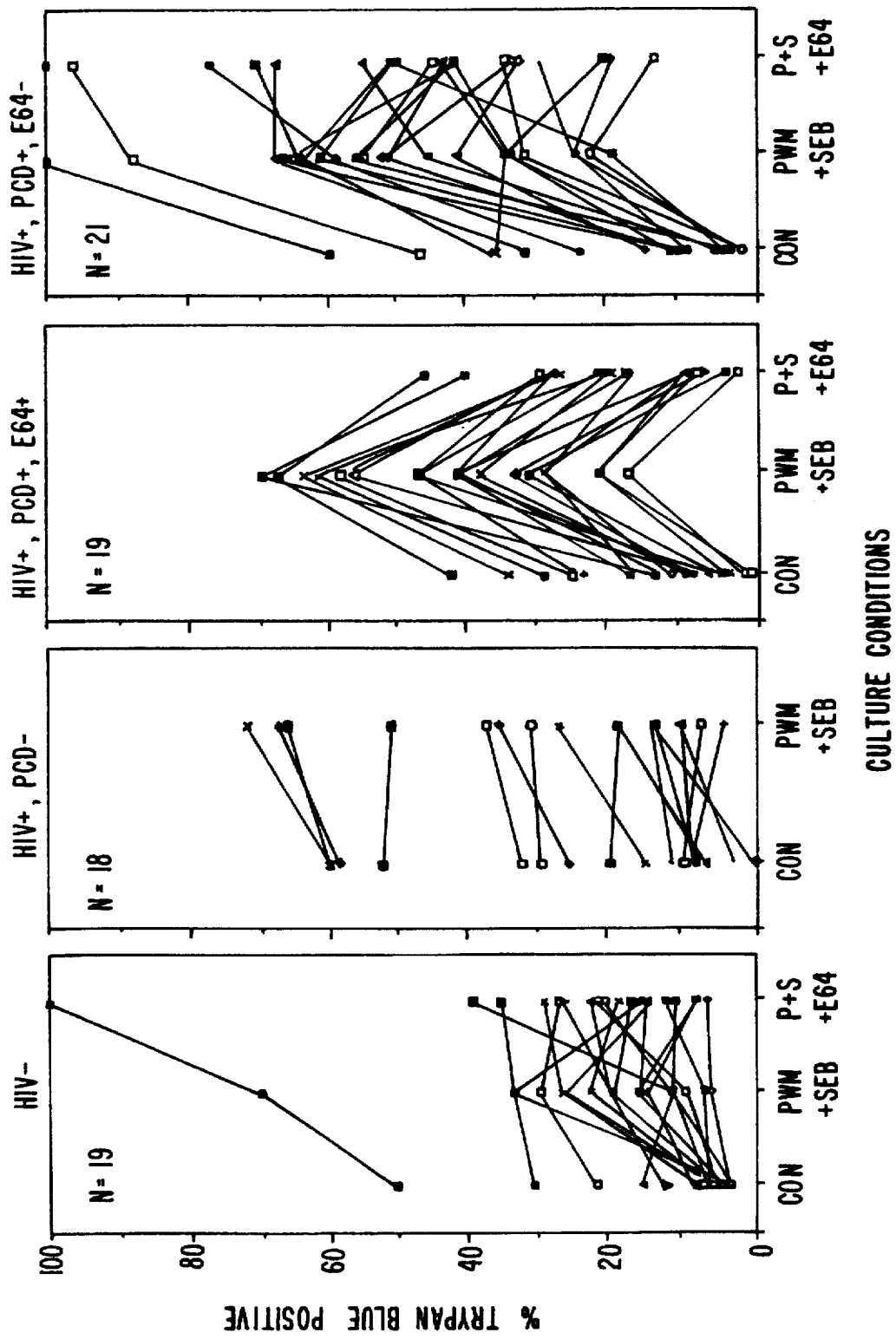
FIG. 7a shows the effect of the cysteine protease inhibitor E-64 on TcR induced PCD in lymphocytes from normal donors and asymptomatic HIV+ donors. The viability by trypan blue exclusion is shown after 48 hour culture in a) control culture with no stimulus ("Con"); b) TcR crosslinking induced by a mixture of pokeweed mitogen (PWM) and staphylococcal enterotoxin B (SEB); and c) same as (b) but with 50 uM E-64. Data shown are for 58 HIV+ asymptomatic donors, and are divided into three groups: The first, PCD⁻, contained 18 individuals in which there was a negligible PCD response; the second group contained 19 donors who showed significant PCD in the presence of these mitogens and whose PCD response was reversed by the presence of E-64; the third group of 21 individuals showed a PCD response which was not reversed by E-64. The "HIV−" panel shows control donors who were treated in the same way as the HIV+ donors. Of the 19 HIV− donors shown here, 5 would have been classified as PCD+ by the definition used for the HIV+ donors.
Figure 7B:
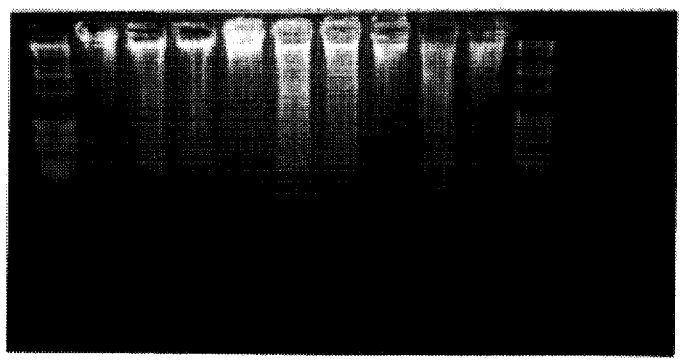
FIG. 7B shows that E-64 reversed apoptotic DNA fragmentation in some HIV+ lymphocytes induced by PWM and SEB. PBMC from three HIV+ donors were cultured as described in FIG. 1A. PCD was seen in all three patients, and reversal by E-64 was marginal in patient #1, modest in patient #2, and substantial in patient #3. Outside lanes contained 1 kb marker DNA.

PCD and the effect of cysteine protease inhibitor was examined in lymphocytes from normal and HIV+ asymptomatic individuals. In these experiments peripheral blood mononuclear cells were cultured for 48 hours with a mixture of pokeweed mitogen (PWM) and the superantigen staphylococcal enterotoxin B (SEB) to induce TcR crosslinking. Cell death was analyzed by a variety of methods, including trypan blue exclusion. The viability by trypan blue exclusion is shown in FIG. 7 after 48 hour culture in complete medium containing 10%FCS in control culture with no stimulus (FIG. 7A; "Con"), with TcR crosslinking induced by a mixture of 10 ug/ml PWM and 10 ug/ml SEB (FIG. 7B), and in cultures with TcR crosslinking and with 50 uM E-64. This E-64 concentration was non-toxic as judged by its lack of effect on control cultures. Data shown are for a total of 58 HIV+ asymptomatic donors (Lucey et al., *J. Infect. Dis.* 164:631 (1991)).

The results are summarized in FIG. 7A and Table 1. The results with HIV+ asymptomatic individuals were divided into three groups. The first, PCD−, contained 18 individuals for whom these stimulation conditions evoked a negligible cell death response. Thus, cells from about 70% of the HIV+ asymptomatic individuals showed clear PCD when cultured under conditions of TcR crosslinking, supporting the involvement of PCD in HIV pathogenesis. The second group contained 19 donors who showed significant PCD in the presence of these mitogens and whose PCD response was reversed by the presence of E-64, where reversal was defined as greater than 50% blocking of the increase in death evoked by TcR stimulation. The third group of HIV+ donors were 21 subjects who showed a PCD response but which were not reversed by E-64 according to the foregoing definition, although about half of them showed some decrease in cell death in response to treatment with E-64. The HIV-panel shows control donors who were treated in the same way as the HIV+ donors. Of the 19 controls shown here, five would have been classified as PCD+ by the definition used for the HIV+ donors. A further quantitative summary of these data is given in Table 1.

TABLE 1

| PCD resronses and reversal by E-64. | | | | | | |
|---|---|---|---|---|---|---|
| | | | NONVIABLE CELLS +/− SEM AFTER CULTURE | | | |
| DONOR TYPE | n | CON-TROL | | +PWM+SEB | | +P+S+E64 |
| HIV− | 20 | 10.5 | 2.8 | 20.7 | 3.3 | 23.7 | 4.6 |
| HIV+ | 59 | 17.6 | 2.1 | 40.7 | 2.7 | 32.6 | 3.0 |
| HIV+PCD− | 17 | 21.5 | 4.7 | 27.2 | 4.8 | 27.0 | 5.2 |
| HIV+PCD+ | 42 | 16.1 | 2.3 | 46.2 | 2.9 | 34.9 | 3.6 |

In addition to viability measurements by trypan blue exclusion, other programmed cell death determinations such as DNA fragmentation measured by agarose gel electrophoresis. PBMC from three HIV+ donors were cultured as described in above. After 48 hours, DNA was prepared from each culture group and electrophoresed in 2% agarose gels containing ethidium bromide. By this criterion, PCD could be seen in all three patients. As shown in FIG. 7B, reversal by E-64 was marginal in patient #1, modest in patient #2, and substantial in patient #3. Outside lanes in FIG. 7B contained Gibco-BRL 1kb marker DNA.

Figures 8A, 8B:
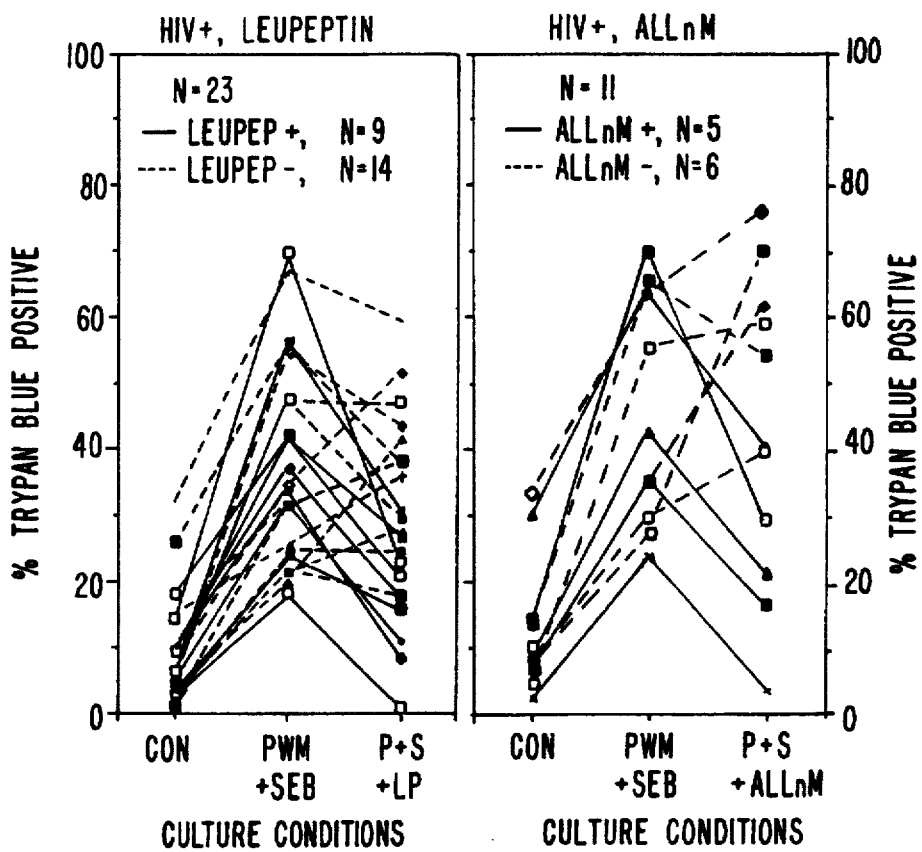
FIG. 8 depicts the effect of the cysteine protease inhibitor leupeptin (left panel; 50 μM) and the calpain inhibitor ALLnM (right panel; 50 μM) on TcR induced PCD in lymphocytes from asymptomatic HIV+ donors.

The effects of the cysteine protease inhibitor leupeptin and the calpain inhibitor ALLnM on TcR induced PCD in lymphocytes from asymptomatic HIV+ donors were also examined. Experimental conditions were the same as described above, with PCD reversal in response to 50 uM leupeptin and 50 uM ALLnM being tested. As shown in FIG. 8, of 23 donors tested with leupeptin, 9 gave significant reversal of PCD, and of the 11 donors tested with the calpain specific inhibitor ALLnM, 5 gave significant reversal.

Overall, the results suggest that a minimum of about 35% of the HIV+ individuals had TcR-induced PCD occurring predominantly via the calpain pathway as described for the murine hybridoma 2B4 in Example I.

The effect of calpain inhibitors on in vitro T cell responses of HIV+ asymptomatic individuals was examined. T cells from HIV+ individuals typically undergo a progressive and irreversible loss of responsiveness to recall antigens, allogeneic cells, and PHA, respectively, as shown by previous studies with both proliferation and IL-2 secretion, and are used to establish criteria for assessing T helper functional status (Clerici et al., J. Clin. Invest. 84:1892 (1989). CD4+ counts increasingly drop as patients progress through this sequence of functional defects (Lucey et al., J. Infect. Dis. 164:631 (1991)), which can be categorized as ——, ——, —T, and ——, according to whether there are responses to the above three T cell stimuli (recall antigens, allogeneic cells, and PHA, respectively). Some of the defective responses could be caused by the relevant T cell clones undergoing a PCD response instead of the normal activation response. The ability of calpain inhibitors to reverse this type of defective response by blocking PCD was examined.

Figures 9A, 9B:
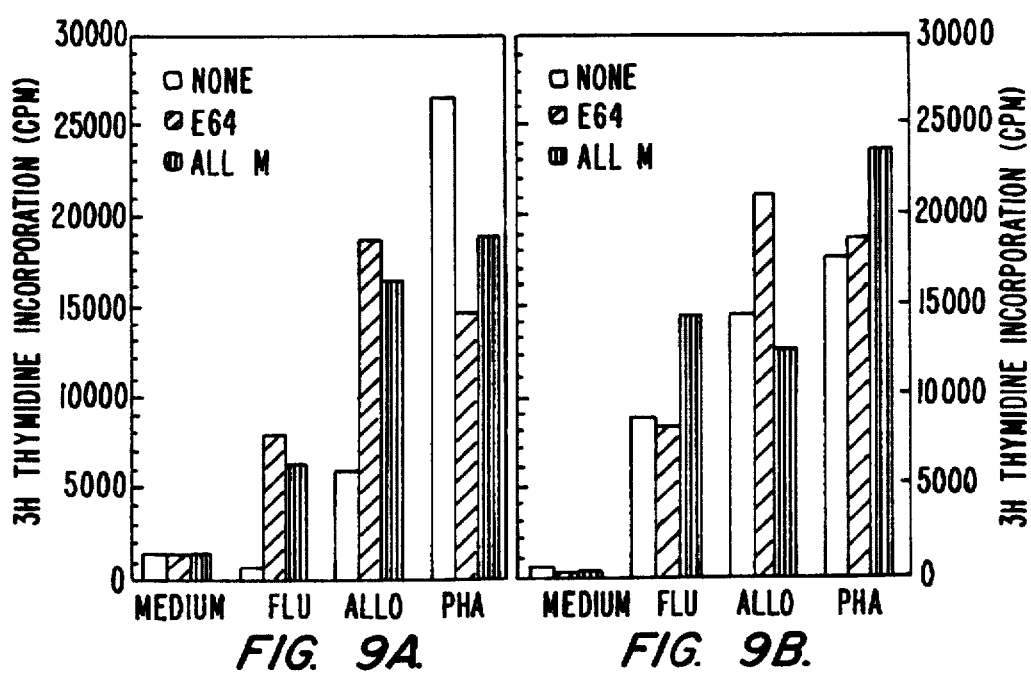
FIG. 9 illustrates the effect of the cysteine protease inhibitor E-64 and the calpain inhibitor ALLnM on T cell proliferative responses of HIV+ asymptomatic donors. Panel A shows an HIV+ asymptomatic donor (functional class ——) in whom there was restoration of the response to the recall antigen influenza (FLU) to near normal levels in the presence of either E-64 or ALLnM. This donor also showed restoration of the response to alloantigen by the two protease inhibitors. Panel B shows an HIV+ asymptomatic donor (functional class +++) whose responses were not significantly affected by the protease inhibitors.

The effects of E-64 and ALLnM on proliferative responses of 52 HIV+ individuals were measured to the influenza recall antigen, allogeneic cells, and to PHA. Three day cultures of PBMC were established with the stimuli indicated as previously described (Clerici et al., J. Clin. Invest. 84:1892 (1989), and the proliferative responses measured using 3 H-thymidine incorporation. In some cases a dramatic restoration of the defective response by calpain inhibitors was observed. As shown in FIG. 9, panel A shows an HIV+ asymptomatic donor in the functional class ---, in whom there was restoration of the response to the recall antigen influenza (FLU) to near normal levels in the presence of either E-64 or ALLnM from the markedly defective response in the absence of drug. This donor also showed restoration of the response to alloantigen by the two protease inhibitors. The protease inhibitors were not mitogenic themselves. Drug effects were scored by taking 3-fold changes in 3 H-thymidine incorporation levels as significant. Panel B of FIG. 9 shows an HIV+ asymptomatic donor (functional class +++) whose response were not significantly affected by the protease inhibitors.

The results with 52 HIV+ donors are summarized in Table 2. Where responses were in the normal range, a large enhancement of the response was not expected, and in the more advanced cases (e.g., the functional class ——) there might have been no influenza-responsive clones remaining and a PCD blocker would not necessarily be expected to restore the response.

A relatively high frequency of restored responses occurred in the most advanced stages of T helper defects. This is the time when CD4+ cell numbers are dropping most rapidly in patients and when the most PCD might be expected. Thus, it can be concluded from these studies that at least some of the loss of T helper function can be attributed to a PCD response replacing a normal activation response in HIV+ asymptomatic individuals.

The effect of protease inhibitors on PCD in murine thymocytes and other cells in vitro was also examined. Calpain inhibitors E64, ALLnM and leupeptin did not block thymocyte PCD in response to steroid, irradiation, or calcium ionophore. Preliminary results suggest that they also do not block TcR-induced PCD in thymocytes, implying that the calpain pathway may be unique to mature lymphocytes. Calpain expression is low in thymocytes, and high in mature lymphocytes (Murachi et al., Biochem. Int. 2: 651 (1981)).

The foregoing results support the use of calpain inhibitors in HIV therapy to exert a selective action on PCD in mature lymphocytes, minimizing some side effects which might occur if calpain inhibitors blocked many types of PCD in other cells.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. An in vitro method for assessing whether individuals infected with human immunodeficiency virus type 1 (HIV-1) are susceptible to cysteine protease-mediated, activation-induced programmed cell death (AI-PCD), comprising the following steps:

(i) obtaining and preparing peripheral blood mononuclear lymphocytes (PBMCs) from HIV-1$^+$ donors;

(ii) polyclonally activating said PBMCs with antigen and/or mitogen to stimulate AI-PCD;

(iii) measuring the percentage of inhibition of AI-PCD in the presence or absence of a cysteine protease inhibitor in said HIV-1$^+$ donors; wherein said inhibition of

TABLE 2

| | Effect on T cell proliferative responses of protease inhibitors E-64 AND ALLnM | | | | | | |
|---|---|---|---|---|---|---|---|
| | T HELPER | | | NUMBER OF RESPONSES CHANGED | | | |
| HIV | FUNCTIONAL | | | >3× INCREASE | | >3× DECREASE | |
| STATUS | CATEGORY | n | Ag | E-64 | AllnM | E-64 | ALLnM |
| + | +++ | 16 | FLU | 0 | 1 | 0 | 1 |
| | | | ALLO | 1 | 2 | 0 | 0 |
| | | | PHA | 1 | 1 | 1 | 0 |
| + | —++ | 22 | FLU | 4 | 6 | 0 | 2 |
| | | | ALLO | 1 | 1 | 0 | 4 |
| | | | PHA | 2 | 3 | 0 | 0 |
| + | —+ | 6 | FLU | 1 | 1 | 0 | 1 |
| | | | ALLO | 2 | 2 | 0 | 0 |
| | | | PHA | 0 | 1 | 0 | 0 |
| + | — | 9 | FLU | 1 | 1 | 0 | 1 |
| | | | ALLO | 4 | 4 | 0 | 0 |
| | | | PHA | 3 | 5 | 0 | 0 |
| − | +++ | 15 | FLU | 0 | 1 | 1 | 0 |
| | | | ALLO | 0 | 0 | 0 | 0 |
| | | | PHA | 0 | 0 | 0 | 0 |

AI-PCD is indicative of said individuals being susceptible to cysteine protease-mediated AI-PCD.

2. The method of claim 1, wherein the percentage of inhibition of AI-PCD in the presence or absence of a cysteine protease inhibitor in said HIV-1$^+$ donors is determined by DNA fragmentation or trypan blue staining assays.

3. The method of claim 1, wherein the antigen employed in the polyclonal activation of PBMCs is a recall antigen or alloantigen.

4. An in vitro method for assessing whether cysteine proteases are capable of restoring antigen- and/or mitogen-dependent T-lymphocyte proliferative responses in individuals infected with the human immunodeficiency virus type 1 (HIV-1) who are susceptible to cysteine protease-mediated, activation-induced programmed cell death (AI-PCD), comprising the following steps:

(i) obtaining and preparing peripheral blood mononuclear lymphocytes (PBMCs) from HIV-1$^+$ donors;

(ii) polyclonally activating said PBMCs with antigen and/or mitogen, either in the presence or absence of a cysteine protease inhibitor; and, (iii) measuring antigen- and/or mitogen-dependent T-lymphocyte proliferative responses; wherein said T-lymphocyte proliferation in the presence of a cysteine protease inhibitor is indicative of restoration of said T-lymphocyte proliferative response.

5. The method of claim 4 wherein said antigen employed in the polyclonal activation of PBMCs is a recall antigen or alloantigen.

* * * * *